US010646119B2

(12) United States Patent
Deane et al.

(10) Patent No.: US 10,646,119 B2
(45) Date of Patent: May 12, 2020

(54) PLAQUE LOCATION DETECTION IN TIME-RESOLVED FLUORESCENCE METHOD AND SYSTEM FOR PLAQUE DETECTION

(71) Applicant: KONINKLIJKE PHILIPS N.V., Eindhoven (NL)

(72) Inventors: Steven Charles Deane, Cambridge (GB); Olaf Thomas Johan Antonie Vermeulen, Oss (NL); Jan Hendrik Poesse, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 4 days.

(21) Appl. No.: 14/903,298

(22) PCT Filed: Jun. 30, 2014

(86) PCT No.: PCT/EP2014/063799
§ 371 (c)(1),
(2) Date: Jan. 7, 2016

(87) PCT Pub. No.: WO2015/003939
PCT Pub. Date: Jan. 15, 2015

(65) Prior Publication Data
US 2017/0000352 A1 Jan. 5, 2017

(30) Foreign Application Priority Data
Jul. 11, 2013 (EP) ..................................... 13176164

(51) Int. Cl.
*A61C 1/08* (2006.01)
*A46B 5/00* (2006.01)
(Continued)

(52) U.S. Cl.
CPC .............. *A61B 5/0088* (2013.01); *A46B 9/04* (2013.01); *A46B 15/0006* (2013.01);
(Continued)

(58) Field of Classification Search
CPC ..... A61B 5/0088; A61B 5/0071; A61B 5/486; A61B 1/07; A46B 9/04; A46B 15/0006; A46B 15/0044; A61C 17/221
(Continued)

(56) References Cited
U.S. PATENT DOCUMENTS 5,818,587 A    10/1998  Devaraj et al.
6,485,300 B1 *  11/2002  Muller ............... A46B 15/0002
                                                                  433/29
(Continued)

FOREIGN PATENT DOCUMENTS

CN    1309545 A    8/2001
CN    1498091 A    5/2004
(Continued)

OTHER PUBLICATIONS

McConnell et al., Time-correlated single-photon counting fluorescence lifetime confocal imaging of decayed and sound dental structures with a white-light supercontinuum source (Year: 2007).*
(Continued)

*Primary Examiner* — Sean M Michalski
*Assistant Examiner* — Mirayda A Aponte

(57) ABSTRACT

A plaque detection system is presented including a dental implement and a multi-mode optical waveguide for receiving fluorescence light from a plurality of angles, the fluorescence light traveling along a core of the multimode optical waveguide at different path lengths resulting in modal dispersion. The plaque detection system also includes a detector configured to receive the fluorescence light for detecting plaque, calculus, and/or caries, and communicat-
(Continued)

ing plaque identification information of teeth based on frequency domain lifetime measurements. The modal dispersion is used to detect at least one plaque, calculus, and or caries fluorescence area on the teeth. The plaque fluorescence area detected with modal dispersion includes different levels of plaque with respect to a center point of the plaque fluorescence area. Thus, a plaque detection signal depends on a radial distance from the center point of the plaque fluorescence area.

12 Claims, 3 Drawing Sheets

(51) Int. Cl.
 A46B 9/04 (2006.01)
 A46B 15/00 (2006.01)
 A61B 1/07 (2006.01)
 A61C 17/22 (2006.01)
 A61B 5/00 (2006.01)
(52) U.S. Cl.
 CPC ............ *A46B 15/0044* (2013.01); *A61B 1/07* (2013.01); *A61B 5/0071* (2013.01); *A61B 5/486* (2013.01); *A61C 17/221* (2013.01)
(58) Field of Classification Search
 USPC ........ 433/29; 15/106; 401/268, 123; 607/79; 362/572–575; 356/73, 247, 601, 608, 356/326; 348/66; 600/109, 245, 246; 382/128–134, 154; 396/16; 606/2; 250/227.2, 234, 370.02, 363.02; 359/17; 358/1.15; 29/896.11
 See application file for complete search history.

(56) References Cited

U.S. PATENT DOCUMENTS

| 2004/0047577 | A1* | 3/2004 | Wang | ................ | G02B 6/02214 385/125 |
|---|---|---|---|---|---|
| 2005/0255424 | A1 | 11/2005 | Hack et al. | | |
| 2007/0111167 | A1 | 5/2007 | Russell et al. | | |
| 2007/0280888 | A1* | 12/2007 | Fujikawa | ............ | A46B 15/0044 424/9.71 |
| 2011/0070561 | A1 | 3/2011 | Fujikawa et al. | | |
| 2011/0134519 | A1 | 6/2011 | Cooper | | |
| 2011/0151409 | A1 | 6/2011 | Binner | | |
| 2011/0318712 | A1* | 12/2011 | Reddy | ................ | A61B 5/0071 433/216 |
| 2015/0010878 | A1* | 1/2015 | Seibel | ................ | G01N 21/645 433/27 |

FOREIGN PATENT DOCUMENTS

| CN | 101214141 A | 7/2008 | | |
|---|---|---|---|---|
| CN | 101249801 A | 8/2008 | | |
| CN | 101262822 A | 9/2008 | | |
| CN | 102106720 A | 6/2011 | | |
| CN | 202458761 U | 10/2012 | | |
| EP | 2338405 A1 | 6/2011 | | |
| JP | 1147166 A | 2/1999 | | |
| JP | 2002515276 A | 5/2002 | | |
| JP | 2004089239 A | 3/2004 | | |
| JP | 2009501579 A | 1/2009 | | |
| WO | 9959462 A1 | 11/1999 | | |
| WO | 02074160 A1 | 9/2002 | | |
| WO | 2007009234 A1 | 1/2007 | | |
| WO | 2011139844 A1 | 11/2011 | | |
| WO | WO 2013109978 A1 * | 7/2013 | ............ | G01N 21/645 |
| WO | 2014097135 A1 | 6/2014 | | |

OTHER PUBLICATIONS

Gerritsen et al: "Fluorescence Lifetime Imaging of Oxygen in Dental Biofilm"; Proceedings of SPIE, vol. 4164, 2000, pp. 70-78.
Hendrickson et al: "Microcavities Using Holey Fibers"; Journal of Lightwave Technology, vol. 25, No. 10, Oct. 2007, pp. 3068-3071.
McConnel et al: "Time-Correlated Single-Photon Counting Fluorescence Lifetime Confocal Imaging of Decayed and Sound Dental Structures With a White-Light Supercontinuum Source"; Journal of Microscopy, vol. 225, No. 2, Feb. 2007, pp. 126-136.
Siegel et al: "Studying Biological Tissue With Fluorescence Lifetime Imaging: Microscopy, Endoscopy, and Complex Decay Profiles"; Applied Optics, Jun. 2003, vol. 42, No. 16, pp. 2995-3004.

* cited by examiner

PLAQUE LOCATION DETECTION IN TIME-RESOLVED FLUORESCENCE METHOD AND SYSTEM FOR PLAQUE DETECTION

CROSS-REFERENCE TO PRIOR APPLICATIONS

This application is the U.S. National Phase application under 35 U.S.C. § 371 of International Application No. PCT/EP2014/063799, filed on Jun. 30, 2014, which claims the benefit of or European Patent Application No. 13176164.5, filed on Jul. 11, 2013. These applications are hereby incorporated by reference herein.

FIELD OF THE INVENTION

The present disclosure relates to dental cleaning implements, such as toothbrushes. More particularly, the present disclosure relates to an electronic toothbrush for detecting plaque based on time-resolved fluorescence.

BACKGROUND OF THE INVENTION

Toothbrushes are designed to clean teeth by removing bio-films and food debris from teeth surfaces and interproximal regions in order to improve oral health. A wide variety of electronic toothbrush designs have been created to provide improved brushing performance by increasing the speed of the brush head and using sonic vibration, and in some cases ultrasonic vibration. Modern toothbrushes are very efficient at removing plaque. The consumer need only brush in the problem area for a few seconds to lift off plaque that is being brushed. However, without feedback the consumer may move on to another tooth before plaque has been completely removed. Thus, an indication of plaque levels on the teeth is highly desirable.

Despite improvements in toothbrush designs, an issue still remains in that existing electrical toothbrushes do not detect the absence or presence of plaque. Therefore, there is an increasing need to develop dental cleaning implements that may identify plaque.

SUMMARY OF THE INVENTION

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In accordance with aspects of the present disclosure, a plaque, calculus, and/or caries detection system is presented. The plaque, calculus, and/or caries detection system includes a dental implement and an optical multimode waveguide or light guide for receiving fluorescence light from a plurality of angles, the fluorescence light traveling along a core of the multi-mode optical waveguide at different path lengths resulting in modal dispersion. The plaque detection system also includes a detector configured to receive the fluorescence light for detecting plaque and communicating plaque identification information of teeth based on frequency domain lifetime measurements. The optical waveguide has a length of at least 20 cm, whereby the modal dispersion is used to detect at least one plaque fluorescence area on the teeth.

According to an aspect of the present disclosure, the optical waveguide is a multi-mode optical fiber or a graded index optical fiber.

According to a further aspect of the present disclosure, the modal dispersion is tuned by varying a length of the optical waveguide.

According to a further aspect of the present disclosure, the plaque fluorescence area detected with modal dispersion includes different levels of plaque with respect to a center point of the plaque fluorescence area.

According to another aspect of the present disclosure, the modal dispersion is most different between the center point of the fluorescence area compared to a periphery of the fluorescence area.

According to yet another aspect of the disclosure, a plaque detection signal depends on a radial distance from the center point of the plaque fluorescence area.

According to a further aspect of the disclosure, the modal dispersion is a constant of modulation frequency. The phase shift and demodulation of a time resolved fluorescent response from the plaque fluorescence area varies based on the modal dispersion and the modulation frequency.

According to another aspect of the disclosure, the optical fiber has a numerical aperture (NA) of 0.48 and a length of 2 meters when a modulation frequency is 40 MHz.

According to yet another aspect of the disclosure, a feedback mechanism is provided for collecting real-time feedback to a user manipulating the dental implement based on the modal dispersion detected and/or a summary to a user at the end of a brush cycle with a visual indication.

According to yet a further aspect of the disclosure, a method of detecting plaque, calculus, and/or caries on teeth via a dental implement is presented. The method includes the steps of providing a multi-mode optical waveguide for receiving fluorescence light from a plurality of angles, the fluorescence light traveling along a core of the multi-mode optical waveguide at different path lengths resulting in modal dispersion and providing a detector configured to receive the fluorescence light for detecting plaque and communicating plaque identification information of teeth based on frequency domain lifetime measurements. The modal dispersion is used to detect the radial distance to at least one plaque fluorescence area on the teeth.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

DETAILED DESCRIPTION OF EMBODIMENTS

Figure 1:
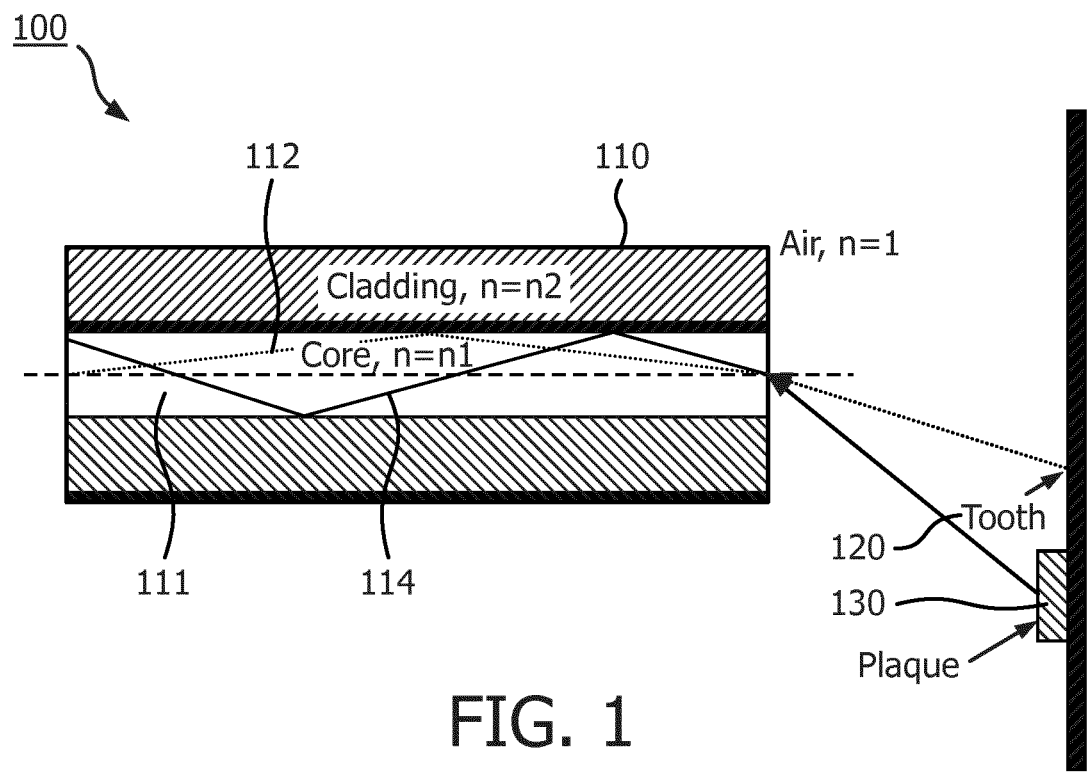
FIG. 1 illustrates a plaque detection system having an optical fiber or waveguide that receives light that takes different times to propagate based on an entrance angle, according to the present disclosure.

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The present disclosure describes various embodiments of systems, devices, and methods for helping users clean their teeth, in particular, by informing users whether they are indeed removing plaque from their teeth and if they have fully removed the plaque, providing both reassurance and coaching the users into good habits. Preferably the information is provided in real-time during brushing/cleaning, otherwise consumer acceptance is likely to be low. For example, it is useful for a dental implement (e.g., a toothbrush or air floss) to provide the user with a signal when the tooth the user is brushing is considered clean, so that the user may move on to the next tooth, which may require additional brushing/cleaning due to plaque build-up. This may reduce the user's brushing/cleaning time, but also leads to a better and more efficient brushing/cleaning routine that focus the user's attention to specific problem areas of the teeth (e.g., that have plaque).

In accordance with the present disclosure, a user is able to detect plaque with an electronic dental cleaning implement, i.e., in a vibrating brushing/cleaning system surrounded with toothpaste foam. The plaque detection system is configured to provide a clear contrast between a surface with the removable plaque layers and a cleaner pellicle/calculus/dental filling/tooth surface.

In accordance with the present disclosure, there is provided a way to detect plaque during the brushing/cleaning routine. The plaque is detected in real-time or substantially close to real-time. The exemplary embodiments of the present disclosure implement plaque detection based on time-resolved fluorescence.

In accordance with the present disclosure, an operation mode is presented for enabling the plaque detection system to detect the radial distance from a center of a detection spot of a plaque residue, while using only one photo-detection system and its associated components. Thus, this disclosure provides further improvements for a way to detect plaque in real-time during the brushing routine by implementing plaque detection based on time-resolved fluorescence, in particular frequency domain lifetime measurements.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments will be described below while referencing the accompanying figures. The accompanying figures are merely examples and are not intended to limit the scope of the present disclosure.

FIG. 1 illustrates a plaque detection system 100 having an optical waveguide 110 that receives light 112, 114 along a core 111 of the optical waveguide 110 that takes different times to propagate based on an entrance angle, according to the present disclosure. The optical waveguide 110 may be a multi-mode optical fiber or a graded index optical fiber.

The present disclosure makes use of an effect seen in multi-mode optical fibers or light guides or waveguides, which leads to mode dispersion. This effect is shown in FIG. 1. Essentially, light 112, 114 may be coupled into the fiber 110 from a range of angles. Designing the fiber 110 to accept light 112, 114 from a wide range of angles typically improves the optical coupling efficiency. However, light entering at a high angle has a longer path 114 length as it travels down the core 111 of the fiber 110, as the coupling angle remains preserved at each reflection event. Over a length of fiber, this different path length 114 can lead to pulse spreading, also referred to as modal dispersion.

In order for the modal dispersion to be exhibited, a minimum length is chosen for the optical waveguide. To this end the optical waveguide (110) has a length of at least 20 cm, which is a distinctly greater length than in the event that optical waveguides are employed in conventional dental implements, such as toothbrushes. In the latter instances, such waveguides are typically present only to bridge a distance between a probe (e.g., at the brush-head of a toothbrush) and a handle. An example of such a toothbrush is illustrated in WO 99/59462.

In the present invention, the length of the optical waveguide preferably is well above the aforementioned minimum, e.g. at least 50 cm (0.5 m). The upper limit of the length of the waveguide will be determined by considerations of design, viz. which lengths can still be accommodated in the dental implement, e.g. by coiling up a fiber-type optical waveguide. The skilled person will be able to determine, for a given dental implement, to balance the considerations of, on the one hand, providing an optical waveguide of relatively large length for exhibiting the modal dispersion, and on the other hand providing an optical waveguide that can be accommodated in a dental implement of a size desirable to the user. In an interesting embodiment the optical waveguide has a length of 0.5 m to 5 m. In an interesting further embodiment, the optical waveguide has a length of 1 m to 3 m.

The effect of modal dispersion also occurs for the fluorescent light collected from the tooth 120 and plaque 130 in the mouth, as it travels back to the photo-detector. This can be utilized to determine the location of the plaque 130. The following description assumes that the plaque 130 is located at a discrete spot, but the methods of the present disclosure also pertain to large areas of plaque, in which case the photo-detector responds to the weighted average of the plaque position.

Figure 2:
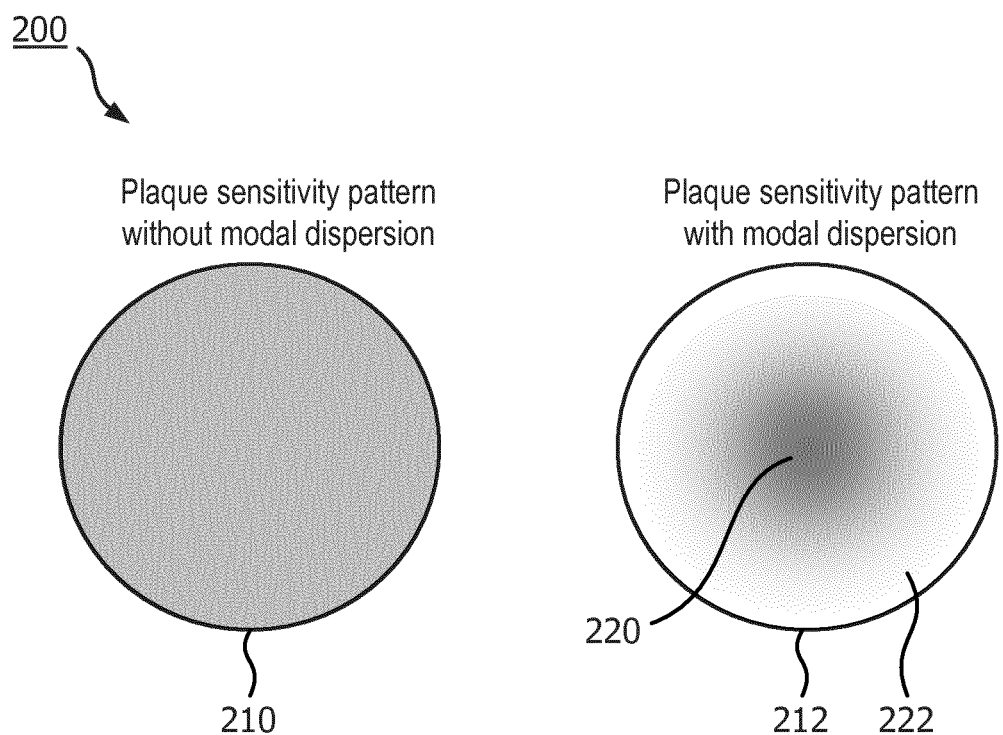
FIG. 2 illustrates examples of plaque sensitivity patterns, according to the present disclosure.

With respect to FIGS. 1 and 2, if it is assumed that a single frequency time-resolved fluorescence system is used, plaque 130 can be detected by its faster fluorescence decay compared to the enamel/dentine of the tooth 120. When considered with modal dispersion, the modal dispersion results in the plaque 130 located at the edge or periphery of the detector spot or area 222 giving a delayed signal, and so appearing more like enamel/dentine. The plaque 130 located near the center 220 of the signal does not experience significant modal dispersion, and, therefore, gives a stronger signal. The strength of the effect of modal dispersion can be tuned by varying the length of fiber 110 used, so as an example, it may be desirable to use a several meter length of fiber 110, even if the distance between a sensor and the detection area 222 is only, for example, a few centimeters. This gives a plaque detection signal depending on radial distance from the center 220 of the detection area 222, in a similar way to the way a metal detector gives the strongest signal when centered over a target. This can be used to facilitate a very intuitive user interaction, where it is easy for the user to understand and detect the plaque location in order to remove it.

FIG. 2 illustrates examples of plaque sensitivity patterns 200, according to the present disclosure.

In FIG. 2, plaque pattern 210 indicates a plaque sensitivity pattern without modal dispersion, whereas plaque pattern 212 indicates plaque sensitivity pattern with modal dispersion. The plaque area 222 includes a central plaque spot 220. Pattern 210 shows the sensitivity pattern that would be normally seen (fairly uniform), while pattern 212 is shown an example of a sensitivity pattern that can be achieved by using modal dispersion effects, as described herein. A darker color (center region) indicates more sensitivity to plaque, while a lighter color (peripheral region) indicates less sensitivity to plaque.

Moreover, if multiple modulation frequencies are used, then the plaque radial distance can be independently measured, as the modal dispersion is a constant of the modulation frequency. However, the phase shift and demodulation of the fluorescent response varies in a different way, due to the typically complex multi-exponential fluorescent decay observed in both plaque and tooth enamel/dentine.

Figure 3A:
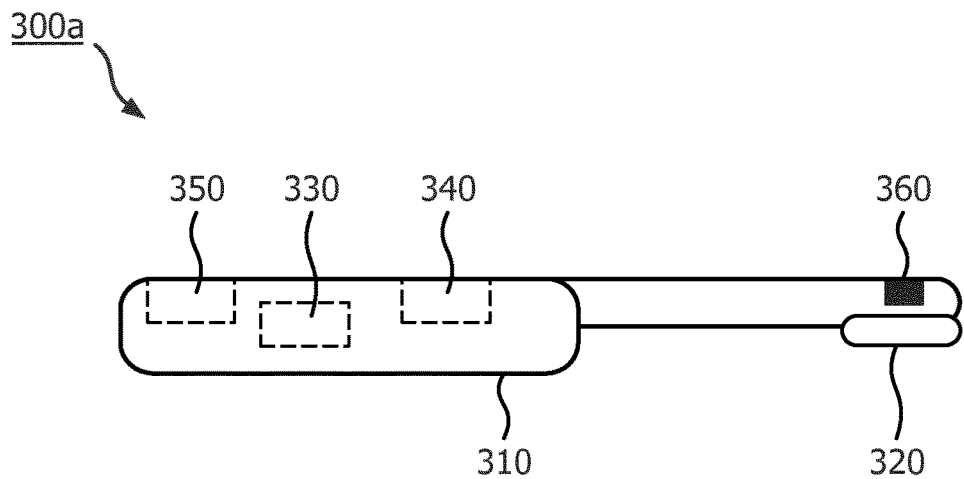
FIG. 3a illustrates a toothbrush, according to the present disclosure.

FIG. 3a illustrates a toothbrush 300a, according to the present disclosure.

The dental implement 300a includes a body portion 310, a brush head 320, a user interface 330, a feedback mechanism 340, and a memory unit or module 350. The feedback mechanism 340 is configured to motivate and coach a user of the dental implement 300a to adapt brushing behavior by providing real-time guidance of the brush head 320. The memory unit 350 is used to store brushing histories of at least one user manipulating the dental implement 300a. The brush head 320 also includes a plaque detection unit 360 (or detector) for detecting an amount of plaque on each tooth. Thus, the feedback mechanism 340 provides for real-time feedback to a user manipulating the dental implement 300a based on the modal dispersion detected and a summary to a user at the end of a brush cycle with a visual indication.

The body portion 310 also included an external interface unit for (wireless) communication with external devices like smart phones, tablets, PCs. The external device can be used for setup of the dental implement and for displaying user feedback and user history.

Figure 3B:
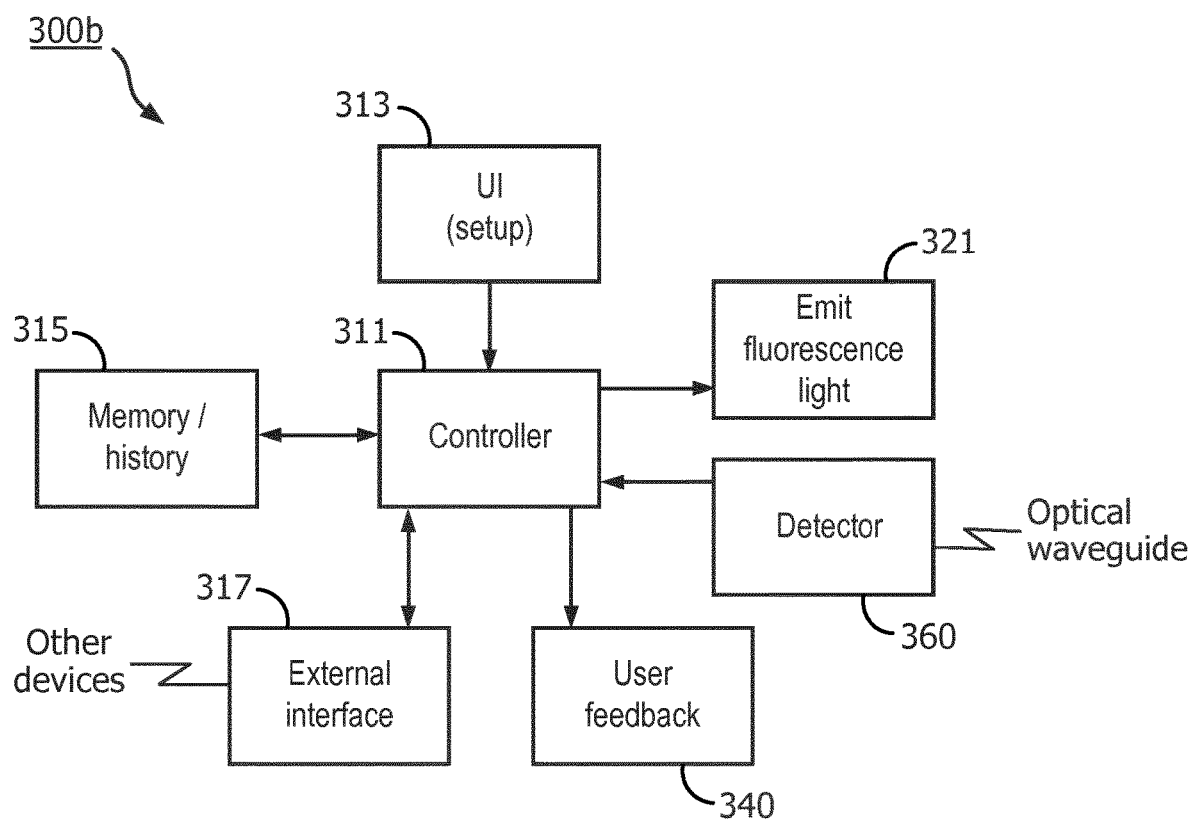
FIG. 3b illustrates a controller environment for the toothbrush of FIG. 3a, according to the present disclosure.

FIG. 3b illustrates a controller environment 300b for the toothbrush of FIG. 3a, according to the present disclosure.

The controller environment 300b includes a controller 311 electrically communicating with a user interface (UI) 313, a memory 315, an external interface 317, the user feedback mechanism 340, and the detector 360. Moreover, the controller 311 may induce an LED or other type of light emitting element to emit light 321 from the dental implement 300a (see FIG. 3a). One skilled in the art may contemplate a plurality of other components within the controller environment 300b.

Figure 4:
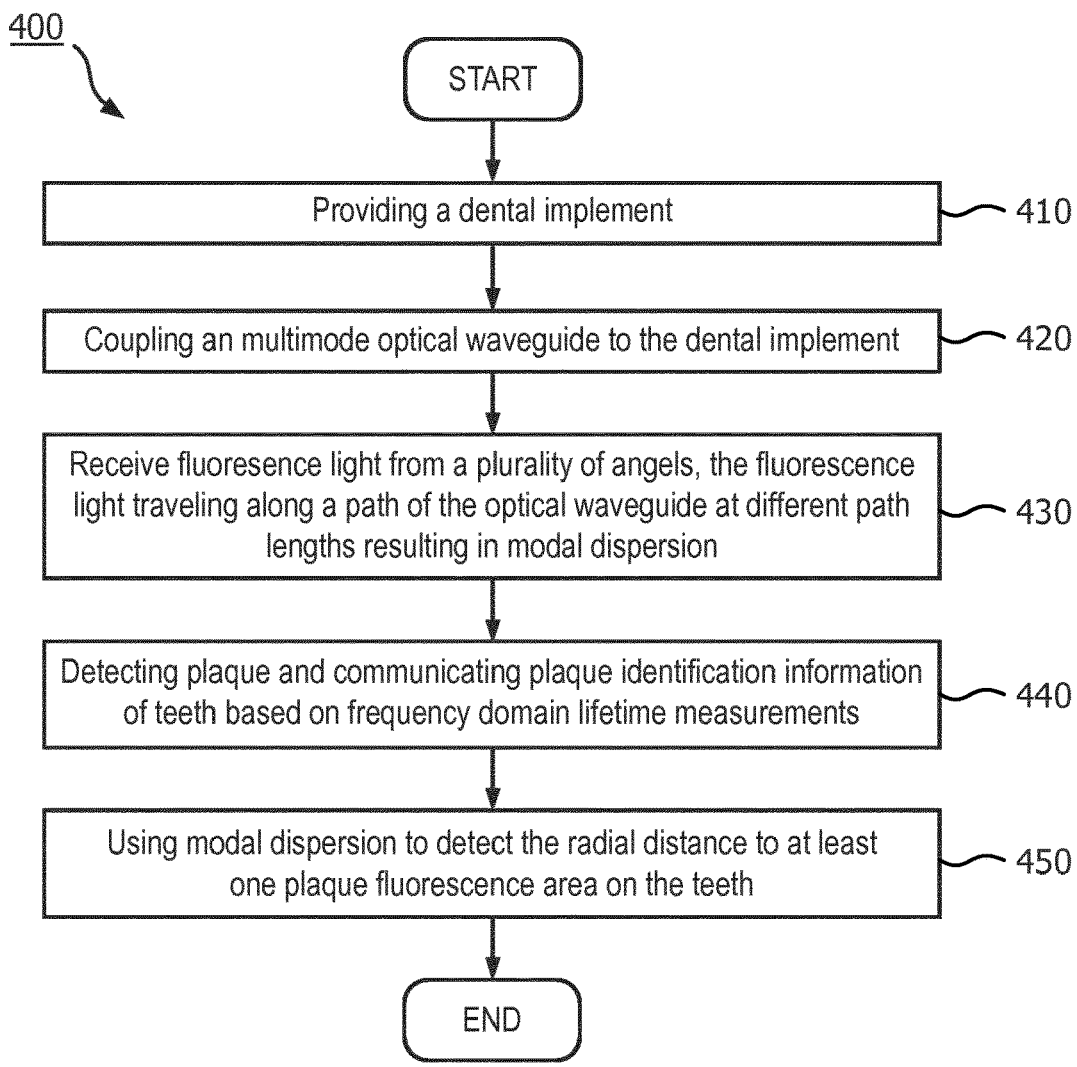
FIG. 4 is a flowchart illustrating a method of detecting the distance to plaque locations based on modal dispersion of a fluorescence lifetime measurement signal, according to the present disclosure.

FIG. 4 is a flowchart 400 illustrating a method of detecting plaque based on a fluorescence lifetime measurement, according to the present disclosure.

The flowchart 400 includes the following steps. In step 410, a dental implement is provided. In step 420, an optical waveguide is coupled to the dental implement. In step 430, fluorescence light is received from a plurality of angles, the fluorescence light traveling along a path of the optical waveguide at different path lengths resulting in modal dispersion. In step 440, plaque is detected and plaque identification information is communicated based on frequency domain lifetime measurements. In step 450, modal dispersion is used to detect the radial distance to the at least one plaque fluorescence area of the teeth. The process then ends. It is to be understood that the method steps described herein need not necessarily be performed in the order as described. Further, words such as "thereafter," "then," "next," etc. are not intended to limit the order of the steps. These words are simply used to guide the reader through the description of the method steps.

With reference to FIGS. 1-4, in one exemplary embodiment, a high numerical aperture (NA) step index optical fiber is used to couple the detection collector to the photo-detector, and this is far longer than physically necessary, for example greater than 1 m long, when the photodiode is <10 cm from the light collection region. The excess fiber can be coiled up and located in the handle of the dental instrument. Other optical transmission means that also exhibit modal dispersion may also be used. If the technique is used alongside motion detection of the brush head, it can be used to build up a map of where the plaque is located in the mouth. Moreover, if 40 MHz modulation is used in the time resolved system, an optical fiber with an NA of 0.48 can be used, and a 2 m length gives phase delay at the edge of the detection spot that roughly cancels the plaque signal. This can achieve the plaque sensitivity map shown in FIG. 2. One skilled in the art may contemplate a plurality of different combinations to achieve desired results and/or outcomes and/or similar effects.

Figure 5:
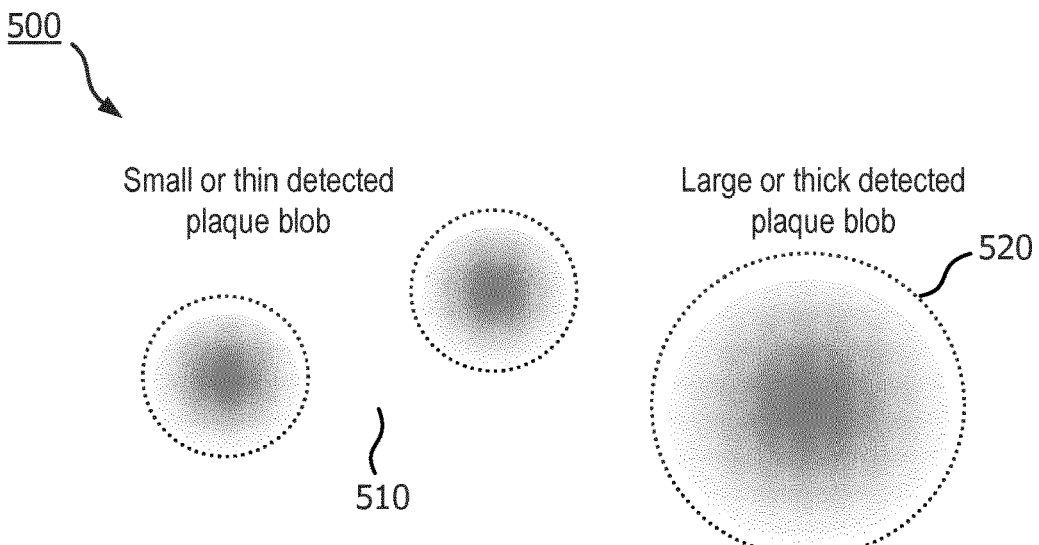
FIG. 5 illustrates examples of detected plaque blobs, according to the present disclosure.

FIG. 5 illustrates examples of detected plaque blobs 500, according to the present disclosure.

In one exemplary embodiment, when the brush head moves along a single tooth of multiple teeth, the size and number of plaque blobs can be recorded. FIG. 5 depicts two blobs. The left blob indicates a small or thin detected plaque blob 510, whereas the right blob indicates a large or thick detected plaque blob 520. This information may be used to give feedback to the user based upon a number of detected parameters, such as, but not limited to, size of the plaque blob, thickness of the plaque blob, closeness to gums, and number of detected plaque blobs during a certain brush head movement.

Based upon the detected parameters, a "signature feedback" may be provided. This "signature feedback" may be audible feedback or vibration feedback, for example, with slight variations in the motor movement of the brush head. Also immediate user feedback may be given with the "signature feedback" when a certain threshold (e.g., like minimum size of plaque blob) is exceeded.

Audible feedback may include a number of pre-recorded audio clues, where each audio clue can give a different indication of the extent, level and/or amount of detected plaque. For instance, different audio clues for scattered small plaque blocks or for larger plaque blobs with are closer positioned together. An audio clue may include special engineered audio patterns which may convey the seriousness of the detected plaque blobs. One skilled in the art may contemplate a plurality of different audio clues based on the desired application.

Moreover, feedback might also be provided to an external device via the external interface unit, described above with reference to FIG. 3b. For example, the feedback may be in the form of one or more real-time visual clues corresponding to the size of the detected plaque blob, as shown in FIG. 5.

Alternatively, at the end of a brushing cycle, a visual indication can be given via a multiple color LED array. When more LEDs light up, the number of positions of detected plaque blobs is larger, while the color of the LEDs can indicate the average (weighted) size of the detected plaque blobs. One skilled in the art may contemplate a plurality of different LED patterns based on the desired application. Moreover, a visual indication might also be provided to an external device via the external interface unit, described above with reference to FIG. 3b.

While this description has been given in terms of frequency domain time-resolved fluorescence, it can also be implemented in time domain time-resolved fluorescence. These methods are related by the well-known Fourier or Laplace transforms, and translation between the two methods is obvious to one skilled in the art. The choice is determined simply by which is more cost effective to implement.

In general, the exemplary embodiments of the present disclosure specifically relate to dental cleaning implements, such as toothbrushes or air floss. However, the exemplary embodiments of the present disclosure may be broadened by one skilled in the art to include professional dental examination devices, whereby presence of plaque may be revealed by images, sound or vibration frequency and intensity. This is applicable in fields such as dentistry, dental hygiene, and tooth whitening.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A detection method, comprising:
emitting fluorescence light from a light emitting element on a toothbrush;
using a multimode optical waveguide having a length of at least 20 cm coupled to the toothbrush and receiving fluorescence light via the multimode optical waveguide from a plurality of angles;
preserving a coupling angle of the fluorescence light within the multimode optical waveguide at at least one reflection event within the multimode optical waveguide;
using a detector configured to receive the fluorescence light from at least one tooth for detecting plaque, calculus and/or caries and communicating plaque identification information of the at least one tooth based on frequency domain lifetime measurements; and
providing real-time feedback to a user of the toothbrush via a feedback mechanism based on modal dispersion used to detect at least one plaque, calculus and/or caries fluorescence area on the at least one tooth and detecting fluorescence light as it travels along a core of the multimode optical waveguide at different path lengths.

2. The detection method according to claim 1, wherein the multimode optical waveguide has a length of 0.5 m to 5 m.

3. The detection method according to claim 1, wherein the step of using the multimode optical waveguide further comprises using a multimode optical waveguide having a length of 1 m to 3 m.

4. The detection method according to claim 1, wherein the plaque, calculus and/or caries fluorescence area detected with modal dispersion includes different levels of plaque, calculus and/or caries with respect to a center point of the plaque fluorescence area.

5. The detection method according to claim 1, wherein the modal dispersion is most different between a center point of the fluorescence area compared to a periphery of the fluorescence area.

6. The detection method according to claim 1, wherein a plaque, calculus and/or caries detection signal depends on a radial distance of the optical waveguide from a center point of the plaque fluorescence area.

7. The detection method according to claim 6, wherein a numerical aperture, a length, and a modulation frequency are chosen so that a phase delay at an edge of a the detection spot substantially cancels the plaque, calculus and/or caries signal.

8. The detection method according to claim 1, wherein the modal dispersion is a constant of modulation frequency.

9. The detection method according to claim 8, wherein a phase shift of a fluorescent response from the plaque, calculus and/or caries fluorescence area varies based on the modal dispersion.

10. The detection method according to claim 1, wherein the step of providing real-time feedback via the feedback mechanism further comprises providing a feedback to a user at the end of a brush cycle with a visual indication.

11. A detection method, comprising:
emitting fluorescence light from a light emitting element on a toothbrush;

using a step index optical fiber waveguide coupled to the toothbrush and receiving fluorescence light via the step index optical fiber waveguide from a plurality of angles;

preserving a coupling angle of the fluorescence light within the multimode optical waveguide at at least one reflection event within the multimode optical waveguide;

using a detector configured to receive the fluorescence light from at least one tooth for detecting plaque, calculus and/or caries and communicating plaque identification information of the at least one tooth based on frequency domain lifetime measurements; and providing real-time feedback to a user of the toothbrush via a feedback mechanism based on modal dispersion used to detect at least one plaque, calculus and/or caries fluorescence area on the at least one tooth and detecting fluorescence light as it travels along a core of the step index optical fiber waveguide at different path lengths.

12. A detection method, comprising:

emitting fluorescence light from a light emitting element on a toothbrush;

using a graded index optical fiber waveguide coupled to the toothbrush and receiving fluorescence light via the graded index optical fiber waveguide from a plurality of angles;

preserving a coupling angle of the fluorescence light within the multimode optical waveguide at at least one reflection event within the multimode optical waveguide;

using a detector configured to receive the fluorescence light from at least one tooth for detecting plaque, calculus and/or caries and communicating plaque identification information of the at least one tooth based on frequency domain lifetime measurements; and providing real-time feedback to a user of the toothbrush via a feedback mechanism based on modal dispersion used to detect at least one plaque, calculus and/or caries fluorescence area on the at least one tooth and detecting fluorescence light as it travels along a core of the grade index optical fiber waveguide at different path lengths.

\* \* \* \* \*